(12) United States Patent
Leopold et al.

(10) Patent No.: US 8,398,700 B2
(45) Date of Patent: Mar. 19, 2013

(54) INTRAVASCULAR FLOW MODIFIER AND REINFORCEMENT DEVICE AND DEPLOYMENT SYSTEM FOR SAME

(75) Inventors: Eric W. Leopold, Redwood City, CA (US); Josef L. Friedmann, Boulder Creek, CA (US); Neal H. Padilla, San Jose, CA (US)

(73) Assignee: Micrus Corporation, Sunnyvale, CA (US)

( * ) Notice: Subject to any disclaimer, the term of this patent is extended or adjusted under 35 U.S.C. 154(b) by 605 days.

(21) Appl. No.: 11/838,149

(22) Filed: Aug. 13, 2007

(65) Prior Publication Data

US 2008/0021535 A1  Jan. 24, 2008

Related U.S. Application Data

(62) Division of application No. 10/699,612, filed on Oct. 31, 2003, now abandoned.

(60) Provisional application No. 60/447,601, filed on Feb. 14, 2003.

(51) Int. Cl.
*A61F 2/84* (2006.01)
*A61F 2/88* (2006.01)

(52) U.S. Cl. ............ 623/1.12; 623/1.2; 623/1.22

(58) Field of Classification Search ........ 623/1.11–1.13, 623/1.15, 1.18–1.2, 1.22, 1.3, 1.32
See application file for complete search history.

(56) References Cited

U.S. PATENT DOCUMENTS

| | | | |
|---|---|---|---|
| 4,553,545 A | 11/1985 | Maass et al. | |
| 4,795,458 A * | 1/1989 | Regan | 623/1.19 |
| 4,913,141 A * | 4/1990 | Hillstead | 623/1.11 |
| 5,183,085 A | 2/1993 | Timmermans | |
| 5,217,483 A | 6/1993 | Tower | |
| 5,405,378 A * | 4/1995 | Strecker | 623/1.12 |
| 5,456,667 A * | 10/1995 | Ham et al. | 604/107 |
| 5,554,181 A * | 9/1996 | Das | 623/1.12 |
| 5,575,816 A | 11/1996 | Rudnick et al. | |
| 5,591,230 A | 1/1997 | Horn et al. | |
| 5,643,312 A | 7/1997 | Fischell et al. | |
| 5,653,727 A | 8/1997 | Wiktor | |
| 5,693,083 A * | 12/1997 | Baker et al. | 623/1.11 |
| 5,772,668 A * | 6/1998 | Summers et al. | 623/1.11 |
| 5,776,142 A * | 7/1998 | Gunderson | 623/1.11 |
| 5,797,952 A * | 8/1998 | Klein | 623/1.12 |
| 5,824,041 A * | 10/1998 | Lenker et al. | 606/195 |
| 5,931,866 A | 8/1999 | Frantzen | |
| 5,964,771 A * | 10/1999 | Beyar et al. | 606/108 |
| 6,015,429 A | 1/2000 | Lau et al. | |
| 6,019,779 A * | 2/2000 | Thorud et al. | 606/198 |
| 6,159,165 A * | 12/2000 | Ferrera et al. | 600/585 |
| 6,165,194 A * | 12/2000 | Denardo | 606/191 |
| 6,168,570 B1 | 1/2001 | Ferrera | |
| 6,171,338 B1 | 1/2001 | Talja et al. | |
| 6,187,034 B1 | 2/2001 | Frantzen | |

(Continued)

FOREIGN PATENT DOCUMENTS

EP  0312852 A1  4/1989

*Primary Examiner* — Elizabeth Houston
(74) *Attorney, Agent, or Firm* — Fulwider Patton LLP

(57) ABSTRACT

A stent includes a cylindrical frame consisting of a series of helical winds containing a pattern of alternating zigzag bends. The frame may be made of resilient wire or from a piece of laser cut hypo tubing by placing the stent over a notched portion of a pusher catheter member, and retained on the pusher catheter member by a release wire threaded through the pusher catheter member and over the stent. The stent may also be deployed by placing the stent over a pusher catheter member having opposing notched portions, and retaining the stent and pusher catheter member in a delivery catheter, which can be withdrawn when stent reaches the site to be treated to release the stent.

20 Claims, 8 Drawing Sheets

U.S. PATENT DOCUMENTS

| | | |
|---|---|---|
| 6,214,042 B1 | 4/2001 | Jacobsen et al. |
| 6,224,626 B1 * | 5/2001 | Steinke ................. 623/1.16 |
| 6,302,893 B1 * | 10/2001 | Limon et al. ............. 606/108 |
| 6,355,060 B1 | 3/2002 | Lenker et al. |
| 6,371,979 B1 * | 4/2002 | Beyar et al. ............. 623/1.12 |
| 6,413,273 B1 | 7/2002 | Baum et al. |
| 6,494,907 B1 | 12/2002 | Bulver |
| 6,514,285 B1 * | 2/2003 | Pinchasik ............... 623/1.22 |
| 6,520,986 B2 * | 2/2003 | Martin et al. ............ 623/1.13 |
| 6,530,949 B2 * | 3/2003 | Konya et al. ............. 623/1.12 |
| 6,551,305 B2 | 4/2003 | Ferrera et al. |
| 6,576,006 B2 | 6/2003 | Limon et al. |
| 6,607,551 B1 * | 8/2003 | Sullivan et al. ........... 623/1.11 |
| 6,629,993 B2 | 10/2003 | Voinov |
| 6,679,980 B1 * | 1/2004 | Andreacchi .............. 204/272 |
| 6,736,844 B1 | 5/2004 | Glatt et al. |
| 2002/0173839 A1 | 11/2002 | Leopold et al. |

* cited by examiner

INTRAVASCULAR FLOW MODIFIER AND REINFORCEMENT DEVICE AND DEPLOYMENT SYSTEM FOR SAME

CROSS-REFERENCES TO RELATED APPLICATION

This is a divisional of U.S. Utility patent application Ser. No. 10/699,612 filed on Oct. 31, 2003, which claims priority to U.S. Provisional Patent Application No. 60/447,601, filed Feb. 14, 2003. Each of these applications is hereby incorporated by reference as if set forth in full herein.

BACKGROUND OF THE INVENTION

1. Field of the Invention

The present invention relates to an intravascular flow modifier and reinforcement device, i.e., a stent, for use within a body vessel, and more particularly, to a stent for use in combination with vasoocclusive devices placed adjacent to an aneurysm for the purpose of occluding the aneurysm and providing reinforcement for the area of the blood vessel in the vicinity of the aneurysm.

2. Description of Related Art

The progress of the medical arts related to treatment of vascular malformations has dramatically improved with the availability of intravascular devices capable of operating entirely within the vasculature. Thus, many highly invasive surgical procedures and inoperable conditions have been treated by the use of an expanding number of devices and procedures designed for those purposes. One particularly useful development in the medical arts has been the ability to treat defects in relatively small arteries and veins, such as those in the neurovascular system, by use of an infusion catheter and the placement of embolic coils and the like in areas where the malformation is likely to cause or has already caused a rupture in the blood vessel. More specifically, it has been found that the treatment of aneurysms by such devices and procedures allows the medical practitioner to avoid otherwise risky medical procedures. For example, when the defect is located in the brain, a great deal of difficulty is involved in treatment of small defects in the blood vessels with conventional surgical techniques. For these reasons, the progress in development of devices to treat such defects has been encouraged and has produced useful results in a wide variety of patients.

One aspect of these surgical treatments is that an aneurysm or other malformation is symptomatic of a general weakening of the vasculature in the area containing the aneurysm, and mere treatment of the aneurysm does not necessarily prevent a subsequent rupture in the surrounding area of the vessel. Moreover, it is often desirable to provide a means to prevent the migration of the vasoocclusive devices, such as coils and the like, out of the aneurysm in the event that the aneurysm has a relatively large neck to dome ratio.

Stents, which are tubular reinforcements inserted into a blood vessel to provide an open path within the blood vessel, have been widely used in intravascular angioplasty treatment of occluded cardiac arteries. In such applications, the stent is inserted after an angioplasty procedure or the like in order to prevent restenosis of the artery. In these applications, the stents are often deployed by use of inflatable balloons, or mechanical devices which force the stent open, thereby reinforcing the artery wall and provide a clear through-path in the center of the artery after the angioplasty procedure to prevent restenosis.

While such procedures may be useful in certain aspects of vascular surgery in which vasoocclusive devices are used, the weakness of the vasculature and the tortuosity of the neurovasculature places limits on the applicability of such stents in procedures to repair neurovascular aneurysms. Furthermore, the use of placement techniques, such as balloons or mechanical expansions of the type often found to be useful in cardiac surgery, are relatively less useful in vasoocclusive surgery, particularly when tiny vessels, such as those found in the brain, are to be treated.

Hence, those skilled in the art have recognized a need for a stent compatible with techniques in vasoocclusive treatment of aneurysms that provides selective reinforcement in the vicinity of the aneurysm, while avoiding any unnecessary trauma or risk of rupture to the blood vessel. The need for a highly flexible stent with structural integrity that both allows for placement without a balloon or mechanical expansion and provides sufficient radial support for weakened arterial walls when in a deployed state has also been recognized. It would also be desirable to have a stent which allowed placement of embolic coils in the aneurysm after the placement of the stent, but which can retain coils placed both before and after the stent is inserted. The present invention provides these and other advantages.

SUMMARY OF THE INVENTION

Briefly, and in general terms, the invention relates to various configurations of stents designed for use in the treatment of aneurysms and ischemic diseases.

The intravascular flow modifier and reinforcement device or stent of the present invention is particularly useful for treatment of damaged arteries having aneurysms and the like, and reinforcement of the area in the vicinity of the areas of the artery to be treated, particularly those areas which are treatable by the use of embolic coils or other embolic devices or agents used to occlude the aneurysm. More particularly, the device of the present invention may be used to reinforce the area in the vicinity of the aneurysm while allowing placement of one or more embolic coils through the gaps in the device, while assisting in the retention of the embolic devices within the aneurysm.

In general, an intravascular flow modifier and reinforcement device or stent constructed according to the invention is formed of superelastic or shape memory material, which, in its deployed configuration comprises a helical series of alternating zigzag bends. The device is radially compressed and retained in a delivery sheath or microcatheter to access the aneurysm location. Upon deployment, the device is placed within the vasculature so that it extends from a position distal of the aneurysm to a position proximal of the aneurysm to be treated. As used herein, the terms "proximal" and "proximal direction" when used with respect to the invention are intended to mean moving away from or out of the patient, and the terms "distal" and "distal direction" when used with respect to the invention are intended to mean moving toward or into the patient. These definitions will apply with reference to apparatus, such as catheters, guide wires, and stents.

The invention relates to an intravascular flow modifier and reinforcement device or stent for use in the intravascular treatment of blood vessels. In a first preferred embodiment, the stent includes a generally cylindrical frame formed of an elongate resilient wire configured as a series of helical windings. In an alternate preferred embodiment, the generally cylindrical frame has a polygonal cross-section in which the frame has one or more straight cross-sectional portions to provide a predetermined desired radial shape and stiffness at various points on the circumference of the stent. Similarly, the pitch cross-section of the windings of the stent may be varied to provide different characteristics to more readily adapt the stent to the portion of the anatomy being treated. In one aspect, the stent consists of a series of between 4 and 8 sharp, alternating zigzag or sinusoidal bends or turns in a rotation of wire. With a helical chevron configuration consisting of four alternating zigzag bends per rotation of wire, the wire extends distally from the proximal end of the stent in a helical pattern with a chevron configuration when viewed from a first direction transverse to the longitudinal axis of the stent, and a reverse chevron or bowed configuration when viewed from a second direction transverse to the longitudinal axis of the stent and approximately 90° rotationally offset from the first direction.

In the first preferred embodiment, the stent is formed from a material having properties that provide it with a predeployed radially compressed configuration and a deployed generally cylindrical configuration. In a detailed aspect of the embodiment, the stent is formed from a material having properties that provide it with a predeployed substantially flattened configuration and a deployed generally cylindrical configuration.

In another aspect, the invention provides a range of stent pitch to provide a wire coverage of the inner surface area of the arterial wall and aneurysm being treated of between 7% and 40%. In another aspect, the angle of the chevrons is less than 120° to promote laminar arterial flow.

The invention also provides for a system and method for deploying an intravascular flow modifier and reinforcement device or stent including a generally cylindrical frame formed of an elongate resilient wire configured as a series of helical windings, for use in the intravascular treatment of a target site in a patient's vasculature. In one embodiment, the stent may be deployed with a substantially tubular pusher catheter member having a tubular main shaft and a notched portion, with one or more notches formed in a side of the pusher catheter member for receiving one or more of the helical windings of the stent. Means are provided for removably retaining the one or more helical windings on the notched portion of the pusher catheter member, with the means for removably retaining being withdrawn from the notched portion of the pusher catheter member when the intravascular flow modifier reinforcement device is positioned at the site in the patient's vasculature to be treated to release and deploy the intravascular flow modifier and reinforcement device at the site in the patient's vasculature to be treated. Typically a plurality of the helical windings of the intravascular flow modifier and reinforcement device are received in each of the notches. In one embodiment, the notched portion includes a plurality of alternating notches and tubular shoulder portions formed in the substantially tubular pusher catheter member. In one embodiment, the means for removably retaining the at least one helical winding on the notched portion of the pusher catheter member includes a release wire threaded through the lumen of the pusher catheter member and over the at least one helical winding to retain the one or more helical windings on the notched portion of the pusher catheter member.

In a presently preferred aspect, the system includes a delivery catheter, and the substantially tubular pusher catheter member and the intravascular flow modifier and reinforcement device received on the notched portion of the pusher catheter member are disposed in the delivery catheter. The delivery catheter can thus be withdrawn along with the release wire from the notched portion of the pusher catheter member when the intravascular flow modifier and reinforcement device is positioned at the site in the patient's vasculature to be treated for delivery of the intravascular flow modifier and reinforcement device to the site in the patient's vasculature to be treated.

In an alternate embodiment of the system and method of the invention for deploying the stent of the invention, the notched portion of the pusher catheter member includes a first plurality of notches on one side of the shaft, and a second plurality of notches on an opposing side of the shaft. In this embodiment, the means for removably retaining the one or more helical windings on the notched portion of the pusher catheter member includes a delivery catheter, and the substantially tubular pusher catheter member and the stent received on the notched portion of the pusher catheter member are disposed in the delivery catheter. In a presently preferred aspect, the delivery catheter has an inner diameter that is only slightly larger than an outer diameter of the pusher catheter member, so as to retain the stent on the pusher catheter member. The delivery catheter is withdrawn from the notched portion of the pusher catheter member when the stent is positioned for delivery of the stent to the site in the patient's vasculature to be treated. Typically individual ones of the notches of the second plurality of notches are offset from corresponding ones of the first plurality of notches.

The devices, systems and methods of the present invention provide important advantages over prior art devices in that they eliminate the necessity for balloon or mechanical placement of devices which can cause unnecessary trauma to the delicate vasculature which has already been damaged by the presence of the aneurysm. The invention additionally provides a flexible device which promotes a non-turbulent flow pattern. For these reasons, the invention is particularly useful to cover and reinforce large neck aneurysms. The presence and design of the alternating zigzag bends enhances the flexibility of the device and enhances the ability of the stent to be flattened and compressed, and to subsequently deploy the stent within the vasculature, an issue of considerable importance if neither balloon nor mechanical placement methods are to be used. The use of a helical pattern increases the structural integrity of the stent and provides sufficient radial support for weakened arterial walls when the stent is in a deployed state.

The present invention also contains numerous advantages over the prior art, including enhanced flexibility and loop strength. These characteristics are controlled by several factors including the diameter of the helical winds, the axial spacing of the winds, the diameter or thickness of the wire or hypo tubing and the angle of the alternating zigzag bend pattern.

The collapsibility of the stent for deployment purposes is a function of material and stent configuration. The use of superelastic and/or shape-memory material in combination with the unique helical pattern allows for the stent to be compressed or flattened and stretched for placement within a sheath or catheter. Thus, the invention provides a wide variety of performance characteristics that can be designed as part of the stent configuration.

While certain features of the invention and its use have been described, it will be appreciated by those skilled in the art that many forms of the invention may be used for specific applications in the medical treatment of deformation of the vasculature. Other features and advantages of the present invention will become apparent from the following detailed description taken in conjunction with the accompanying drawings, which illustrate by way of example, the principles of the invention.

DETAILED DESCRIPTION OF THE PREFERRED EMBODIMENTS

As shown in the exemplary drawings, which are provided for the purposes of illustration and not by way of limitation, the intravascular flow modifier and reinforcement device or stent of the present invention is designed to be deployed intravascularly without the necessity of balloons or other expansive elements. The intravascular device of the present invention is particularly useful for treatment of damaged arteries incorporating aneurysms and the like, particularly those which are treatable by the use of embolic coils or other embolic devices or agents used to occlude the aneurysm. More particularly, the device of the present invitation may be used to reinforce the area in the vicinity of the aneurysm while allowing placement of one or more embolic coils through the gaps in the device, while assisting in the retention of the embolic devices within the aneurysm.

In general, an intravascular flow modifier and reinforcement device or stent constructed according to the invention is formed of superelastic or shape memory material, which, in its deployed configuration comprises a helical series of alternating zigzag bends. The device is radially compressed and retained in a deliver sheath or microcatheter to access the aneurysm location. Upon deployment, the device is placed within the vasculature so that it extends from a position distal to a position proximal of the aneurysm to be treated.

Figure 1:
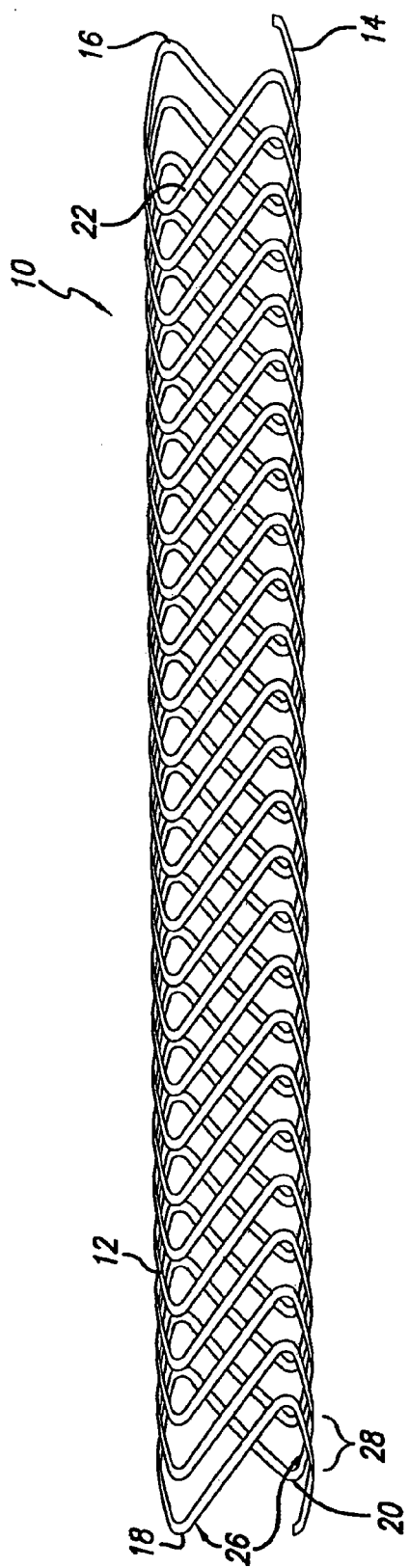
FIG. 1 is a perspective view of a stent in a deployed state and configured in accordance with one embodiment of the invention, having a four alternating zigzag bends per wind configuration.
Figure 2:
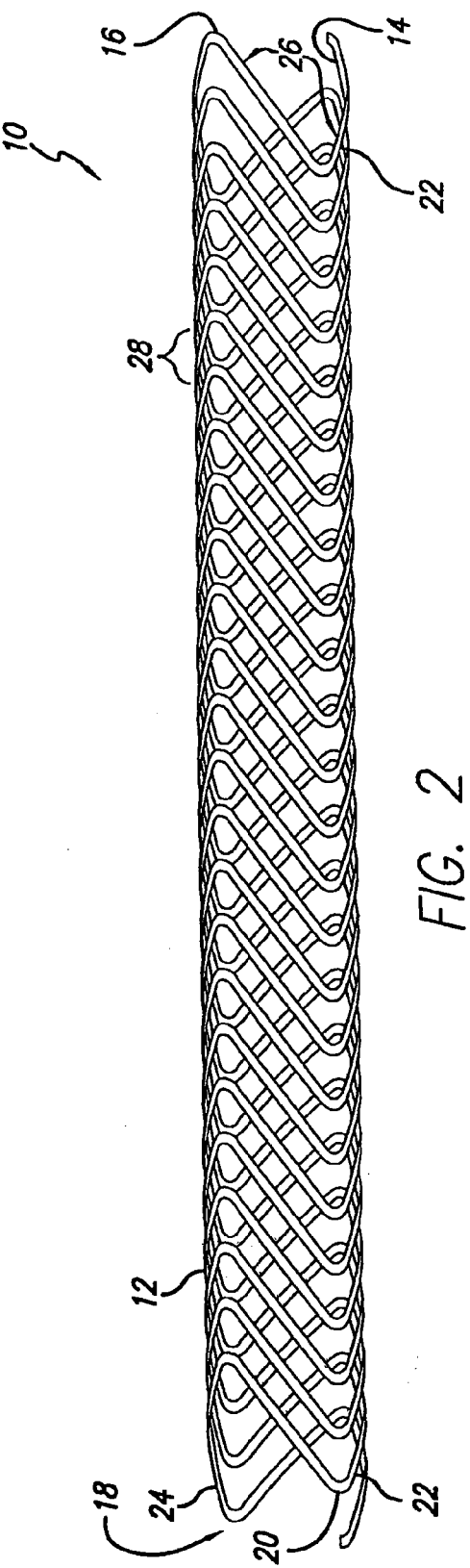
FIG. 2 is a view of the deployed stent of FIG. 1 rotated 90° from the view of FIG. 1.
Figure 6:
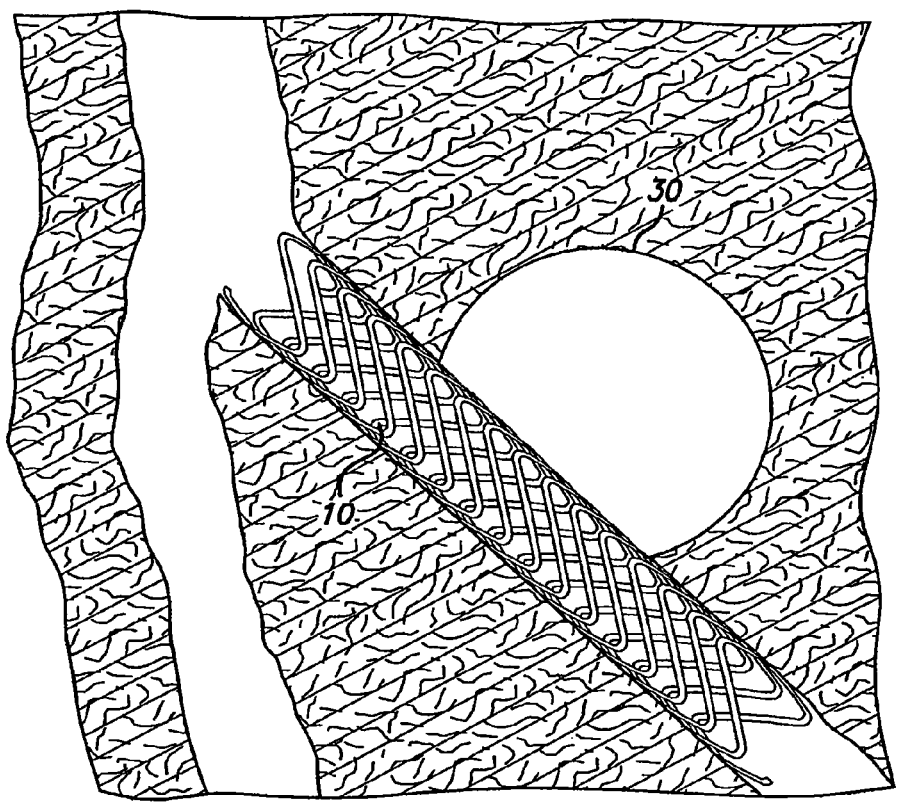
FIG. 6 is a cross section of a vessel with the stent of FIG. 1 deployed in the vicinity of a berry shaped aneurysm.
Figure 7:
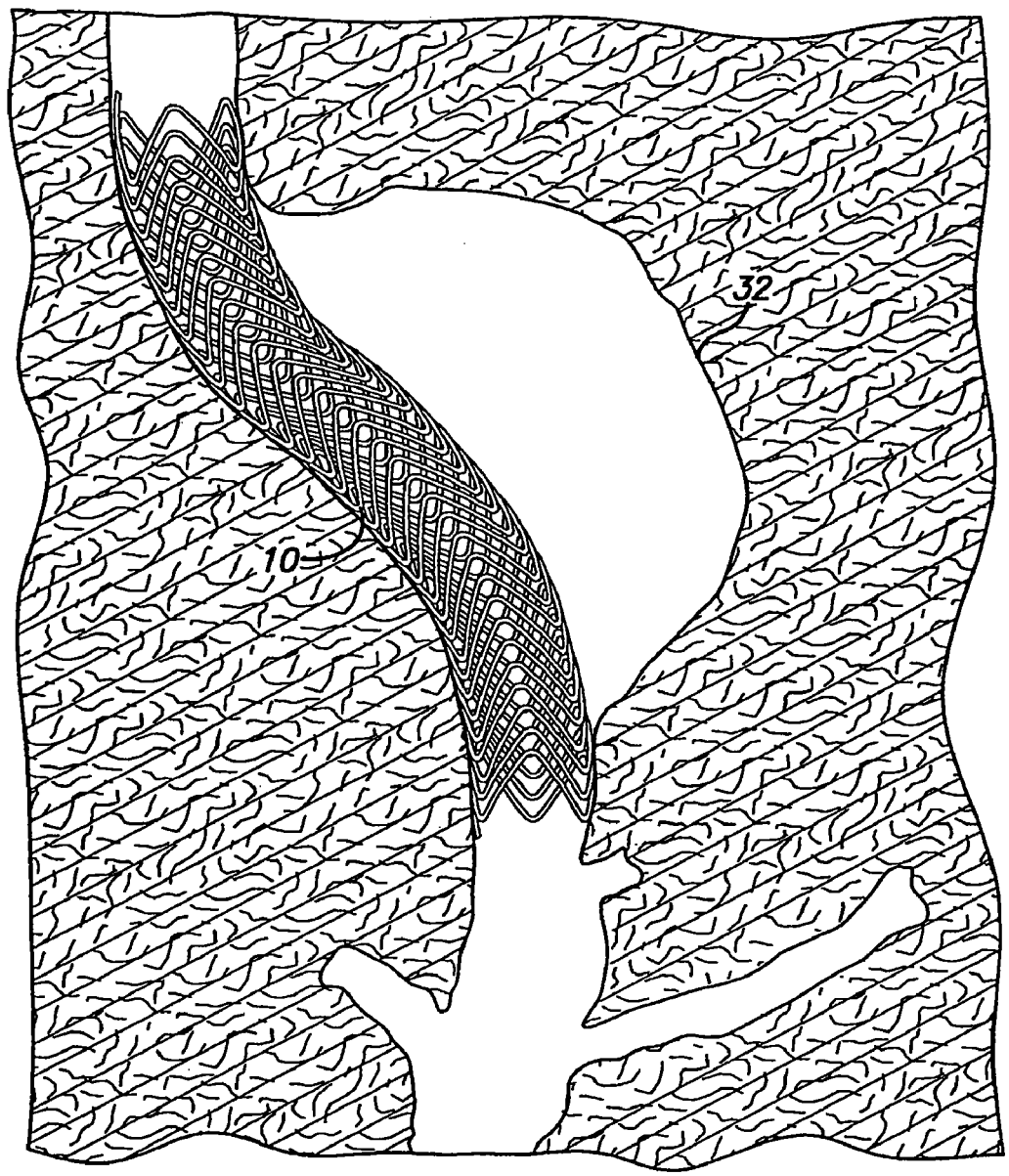
FIG. 7 is a cross section of a vessel with the stent of FIG. 3 deployed in the vicinity of a fusiform type aneurysm.

Turning now to the drawings, in which like reference numerals are used to designate like or corresponding elements among the several figures, in FIGS. 1 and 2, there is shown one embodiment of an intravascular flow modifier and reinforcement device 10, i.e., stent, for use in vasoocclusive procedures. The stent includes a generally cylindrical frame 12 formed of an elongate resilient wire 14 configured as a series helical windings. The wire extends distally from a proximal end 16 of the stent to a distal end 18 of the stent in a helical pattern of sharp alternating, zigzag or sinusoidal bends or turns 20 formed as chevrons 22 and reversed chevrons or bows 24, each having an angle 26 and a spacing or pitch 28. Referring to FIGS. 6 and 7, upon deployment, the stent is placed within the vasculature so that it extends from a position distal to a position proximal of the aneurysm 30, 32 to be treated.

In one aspect of the invention, the stent typically consists of a series of between 4 and 8 bends in a rotation of wire. In FIGS. 1 and 2, the stent consists of a series of four alternating zigzag bends per helical winding.

With the helical alternating zigzag bend configuration consisting of four alternating zigzag bends per rotation of wire, the wire extends distally from the proximal end of the stent in a helical pattern with a chevron configuration when viewed from a first direction transverse to the longitudinal axis of the stent, and a reverse chevron or bowed configuration when viewed from a second direction transverse to the longitudinal axis of the stent and approximately 90° rotationally offset from the first direction.

Figure 3:
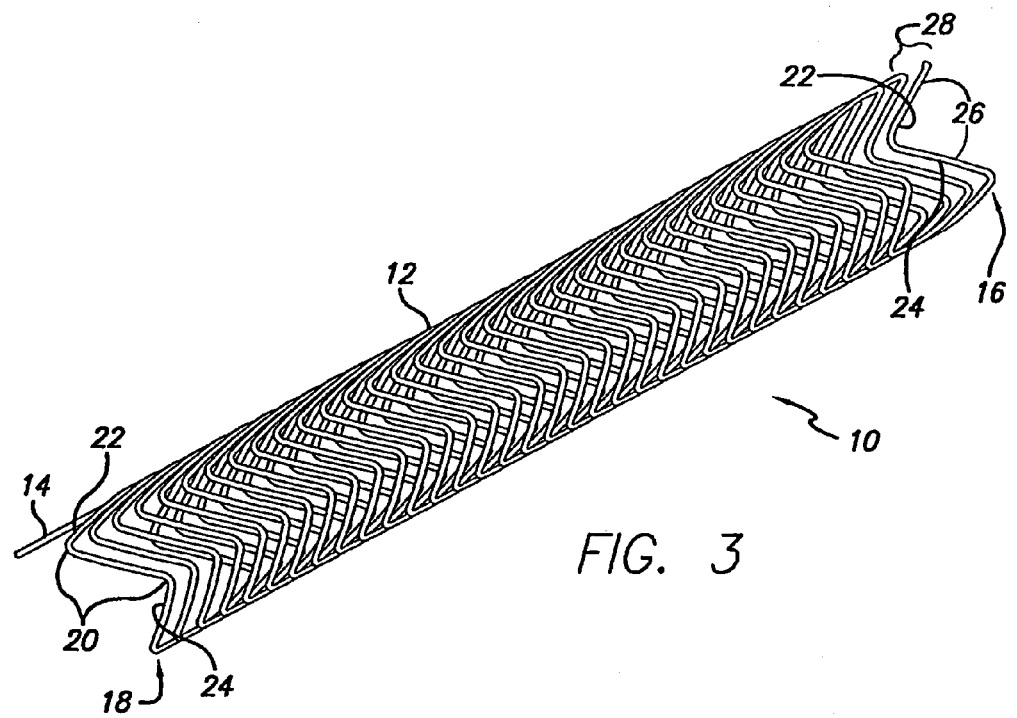
FIG. 3 is a perspective view of a deployed stent illustrating an alternate configuration in which each wind consists of 6 alternating zigzag bends.
Figure 4:
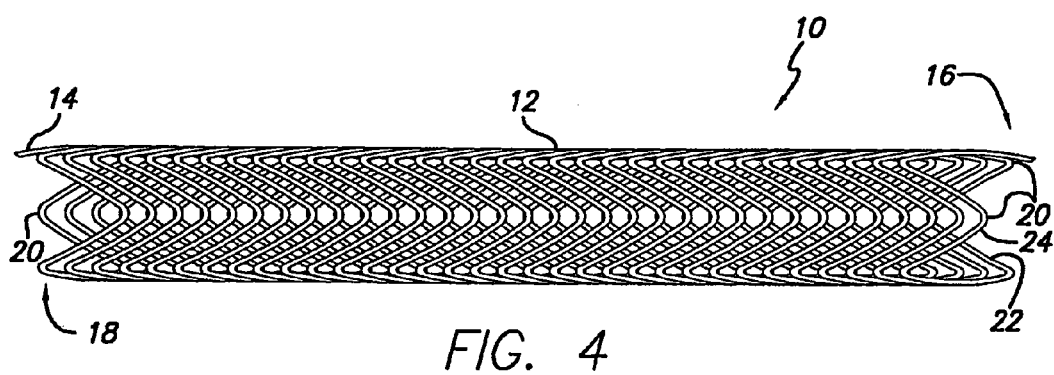
FIG. 4 is a side view of the deployed stent of FIG. 3.

With reference to FIGS. 3 and 4, in one configuration of the stent, the frame is formed from at least one piece of wire configured as a series of helical windings consisting of a series of six alternating zigzag bends.

While the form for making the stent is shown in the figures to be cylindrical, in another aspect of the invention, the form can have a polygonal or non-circular cross-section to provide different radial tension and/or vectoring capabilities for the stent when it is installed. Similarly, the form can be non-cylindrical in the longitudinal axis, generally providing characteristics to match various anatomical configurations to be treated. In a further aspect of a preferred embodiment, the pitch of the windings of the stent may be altered longitudinally to allow for different radial stiffness in the installed stent and to permit vasoocclusive microcoils to be inserted more easily into the aneurysm or malformation being treated.

In another aspect of the invention, the wire of the stent is typically made of a superelastic material such as a nickel-titanium alloy to allow for easy insertion of the radially compressed stent within a sheath or microcatheter. The wire may be coated with a corrosion resistant material such as Parylene or treated by a process such as chemical electropolishing to maximize corrosion resistance. Other materials, such as shape-memory alloys, may also be used to provide for the dual purposes of ease of insertion into a sheath or microcatheter and formation upon deployment into the desired shape of the device. One material that is contemplated as a wire from which the stent can be made is a stranded cable including one or more radiopaque strands, or which has radiopaque markers deployed along its length. Such a stranded cable can be made of a variety of materials including stainless steel, shape-memory alloy, superelastic ally, platinum or the like or combinations thereof. While this configuration of the stent is shown in the form of a cylindrical wire, those skilled in the art will realize that other configurations of material may be used to form the stent, including laminates, flattened wires and laser cut hypo tubing, each of which are within the scope of the invention.

An alternate embodiment of the pre-deployed stent consists of materials, such as shape-memory alloys, which provide for the dual purpose of ease of insertion into a guiding catheter or microcatheter and formation upon deployment into the desired shape of the device.

In an alternate embodiment of the deployed stent configuration not shown, the stent may have a variable pitch or spacing of the helical windings to provide relatively higher density of stent coverage within the aneurysm to support vasoocclusive devices. Alternatively, decreased coverage can be provided in the vessel outside of the aneurysm location to minimize impact on potential perforators. Such configurations have numerous benefits depending on the topology of the damage to the artery, and can provide benefits for certain types of treatment therapies. The stent may be formed in various different configurations. For example, in one configuration the density of the helical winds can be varied from the proximal to the distal end in order to provide a relatively greater density in an area to be placed in a portion of the vasculature that is particularly weak or is threatened by treatment.

As another example (not shown), the stent may be configured to have a variable diameter in the helical windings over the length of the stent in order to provide relatively greater circumferential tension against the wall of the vessel in some areas than others. As another example, the diameter of the helical winds can be increased at certain sections of the stent, for example, the end regions, and thus provide a higher degree of circumferential tension against the wall of the vessel in specific regions. Such a configuration has numerous benefits depending on the topology of the damage to the artery, and can provide benefits for certain types of treatment therapies. Other arrangements are possible. For example, the diameter may taper down in size from both ends of the stent toward the middle. Any of the preceding configurations allow the stent to modify the blood flow characteristics in the vessel in which the stent is deployed.

In one embodiment, the stent, prior to deployment in a vessel, can be compressed into an essentially flat configuration in which one end, such as the proximal end 16 of the stent, is connected to a deployment device on the distal end of a pusher member which fits within a catheter (not shown). In this configuration, the stent has increased flexibility, decreasing the potential of kinking during delivery of the stent to the delivery site.

Figure 5:
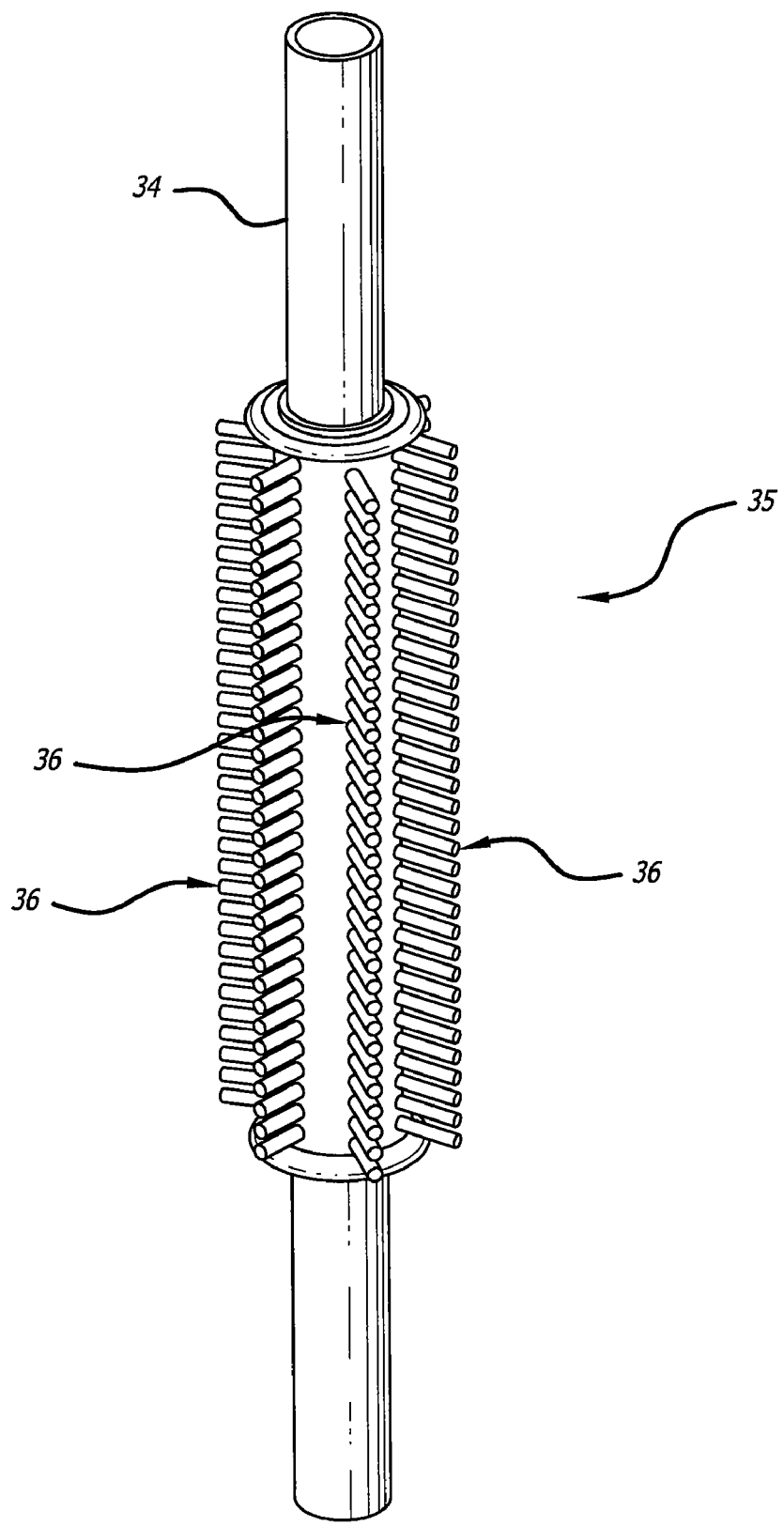
FIG. 5 is an illustration of a mandrel upon which the stent of FIG. 1 is formed in one preferred embodiment of the method of manufacture.

This configuration of the stent may be formed in a number of ways, but there are presently two preferred methods of manufacture. In a first preferred method illustrated in FIG. 5, a longitudinal cylindrical mandrel 34 made of tungsten, ceramic, stainless steel or other heat resistant material has inserted into it pegs 36 of heat resistant material around which the wire to be formed into the stent is wound. The position of the pegs represents transitions along the helical wind generating the alternating zigzag bends. The diameter of the pegs and the spacing of the pegs may be altered in order to provide certain characteristics that are desired in the stent as it is formed. Alternatively, the mandrel can have a grooved configuration formed into it in which the wire is placed prior to heat treatment.

In either method, a single wire is wound progressively down the mandrel forming helical winds until a desired length of the stent is reached. The wire can then be heat treated on the mandrel to create a shape memory or treated to reach a superelastic state.

After formation, the stent is removed from the mandrel. Thereafter, radiopaque markers are loaded and secured to the stent and the stent can be stretched radially compressed to be inserted into a sheath or microcatheter prior to insertion into the vasculature.

The resilience of the wire, in combination with the alternating zigzag bend, or chevron and reversed chevron or bow configuration, allows for transition between a predeployed radially compressed configuration and a deployed generally cylindrical configuration, as shown in FIGS. 1 and 3. When radially inward pressure is applied to the stent, adjacent alternating chevron and reversed chevron or bow sections of the stent collapse toward each other. Accordingly, when the stent experiences radially inward pressure on each of the top, bottom and opposite lateral sides of the stent, the stent compresses in size radially. The reduction in radial size allows for placement of the stent in a microcatheter or sheath without having to flatten and stretch the stent as previously described.

In another embodiment of the invention (not shown), a stent is formed by laser cutting a piece of hypo tubing to form the pattern. The hypo tubing may be formed from a shape-memory material similar to that of the resilient wire of the previous configuration.

The invention provides numerous important advantages in the treatment of vascular malformations, and particularly malformations which include the presence of aneurysms. Since the stents do not require the use of a balloon or other mechanical device for deployment, they are capable of deployment from a small sheath or catheter which need not occlude the artery as it is put into a position from which to deploy the stent. Furthermore, the stents upon deployment can reinforce the artery without occluding access to the aneurysm, thus allowing the stents to be deployed prior to the placement of embolic coils or the like in the aneurysms. Alternatively, depending on the nature of the vascular defect, the embolic coils or other embolic occlusive or other vasoocclusive devices can be placed and the stents deployed thereafter to hold the devices in the aneurysm.

The present invention also contains numerous advantages over the prior art, including enhanced flexibility and loop strength. These characteristics are controlled by several factors including the diameter of the helical winds, the axial spacing of the winds, the diameter or thickness of the wire or hypo tubing and the angle of the alternating zigzag bend pattern.

The collapsibility of the stent for deployment purposes is a function of material and stent configuration. The use of superelastic and/or shape-memory material in combination with the unique helical pattern allows for the stent to be compressed or flattened and stretched for placement within a sheath or catheter. Thus, the invention provides a wide variety of performance characteristics that can be designed as part of the stent configuration.

With references to FIGS. 6 and 7, two configurations of stents are shown deployed within a vessel in the vicinity of an aneurysm. As shown, the alternating zigzag bends configuration of the helical winds cause the stent to expand and fit tightly against the interior wall of the vessel. The compliance of the stent allows for the stent to expand to a generally uniform diameter along its length without entering into the area of the aneurysm. Thus the stent provides support for the vessel in the area around the aneurysm while leaving room for the introduction of embolic coils into the aneurysm.

Figure 8:
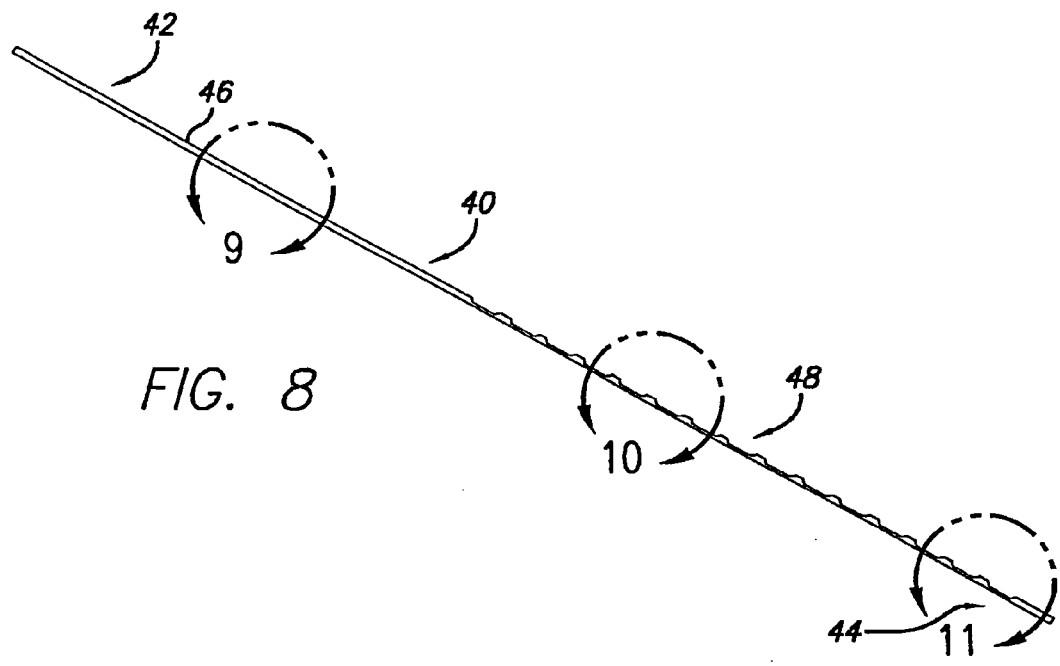
FIG. 8 is an elevational view of a pusher catheter member for deployment of the stent according to the invention.
Figure 9:
FIG. 9 is an enlarged view of section 9 of the pusher catheter member of FIG. 8.
Figure 10:
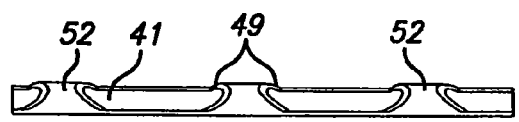
FIG. 10 is an enlarged view of section 10 of the pusher catheter member of FIG. 8.
Figure 11:
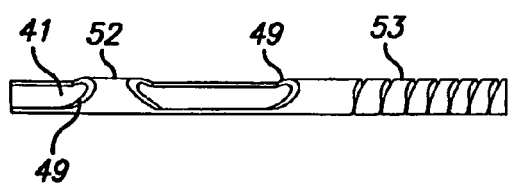
FIG. 11 is an enlarged view of section 11 of the pusher catheter member of FIG. 8.

As is illustrated in FIGS. 8-14, in another aspect of the invention, the stent may be deployed with a substantially tubular pusher catheter member 40 having an inner lumen 41, a proximal portion 42 and a distal portion 44, a tubular main shaft 46 shown in FIGS. 8 and 9, a notched portion 48, with one or more notches 49 formed in a side 50 of the pusher catheter member, as is illustrated in FIGS. 8, 10 and 11. The notched portion is preferably formed with several notches, such as five or more notches, for example, leaving alternating notches and short tubular shoulder portions 52, and the notched pusher catheter is currently preferably formed of a nickel-titanium alloy, such as that available under the trade name NITINOL, for example. The distal portion terminates in a short tubular shaft 53, as is shown in FIGS. 8 and 11.

Figure 12:
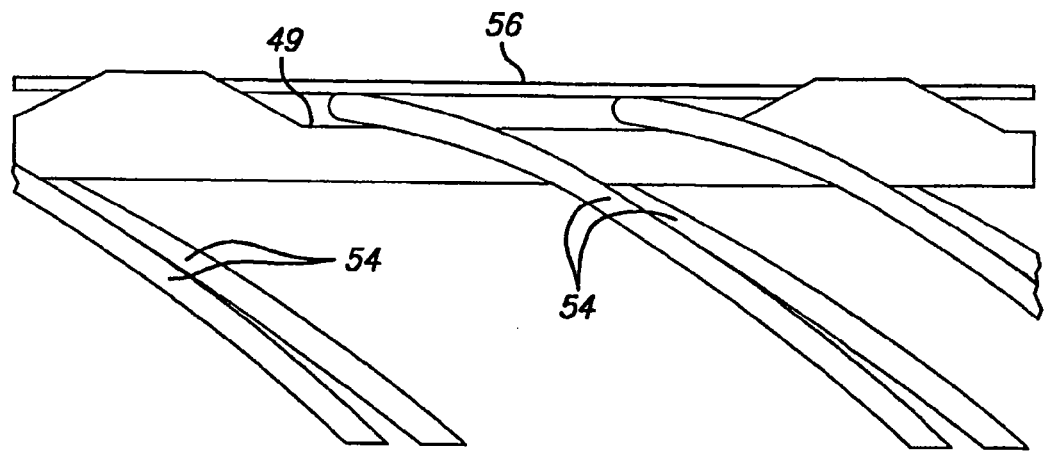
FIG. 12 is an enlarged elevational view of the section 10 of the pusher catheter member of FIG. 10, showing coils of a stent according to the invention captured by a release wire threaded through the pusher catheter member.
Figure 13:
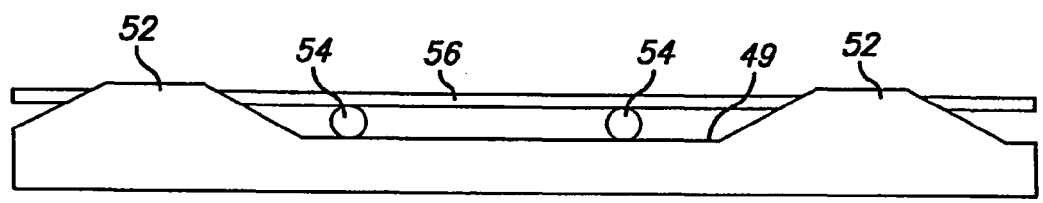
FIG. 13 is a cross-sectional view of the pusher catheter member, coils and release wire of FIG. 12.
Figure 14:
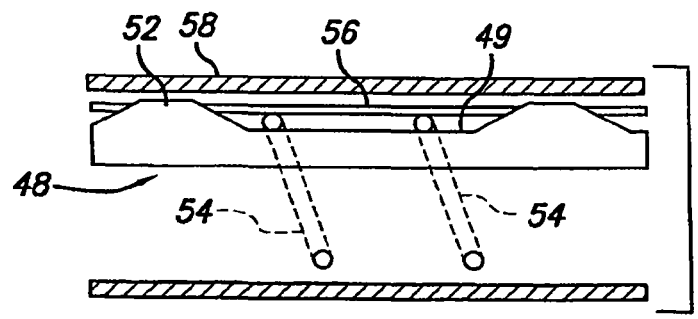
FIG. 14 is a cross-sectional view similar to that of FIG. 13, illustrating delivery of a stent according to the invention via a delivery catheter.
Figure 15:
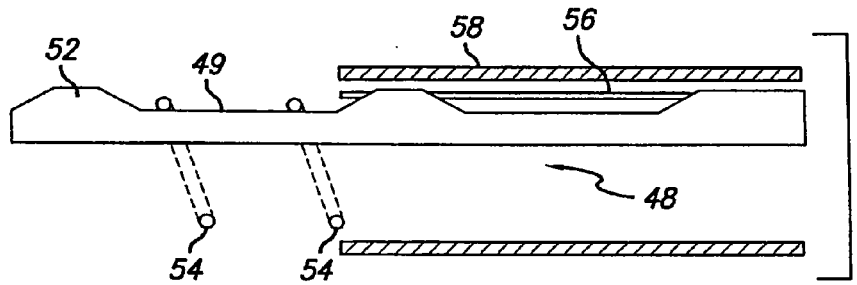
FIG. 15 is a cross-sectional view similar to that of FIG. 14, showing release of the stent.

Referring to FIGS. 12-14, one or more of the helical windings 54 of the stent can be placed over the notches of the pusher catheter member, and typically one to three helical windings may be received in each notch. A release wire 56 can be threaded through the lumen of the pusher catheter member, under the short tubular shoulder portions of the notched portion, and over the helical windings of the stent, to retain the stent on the pusher catheter member. The release wire typically extends from the notched portion of the pusher catheter member to the proximal portion of the pusher catheter member, where the release wire can be manipulated. The release wire is currently preferably formed of a nickel-titanium alloy, such as that available under the trade name NITINOL, for example. As shown in FIG. 14, the pusher catheter member, with the stent loaded onto the notched portion of the pusher catheter member, can be advanced via a delivery catheter 58 or guiding catheter through the vasculature of a patient to a site of an aneurysm to be treated. When the stent is located at the site to be treated, the delivery catheter and release wire can be withdrawn from the notched portion of the pusher catheter member to release and deploy the stent at the site to be treated, as is shown in FIG. 15.

Figure 16:
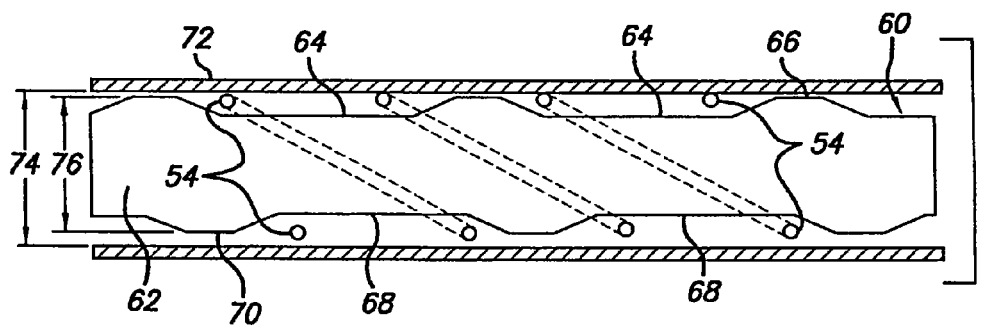
FIG. 16 is a cross-sectional view showing an alternate form of a pusher catheter member with the stent according to the invention mounted thereon in a delivery catheter.
Figure 17:
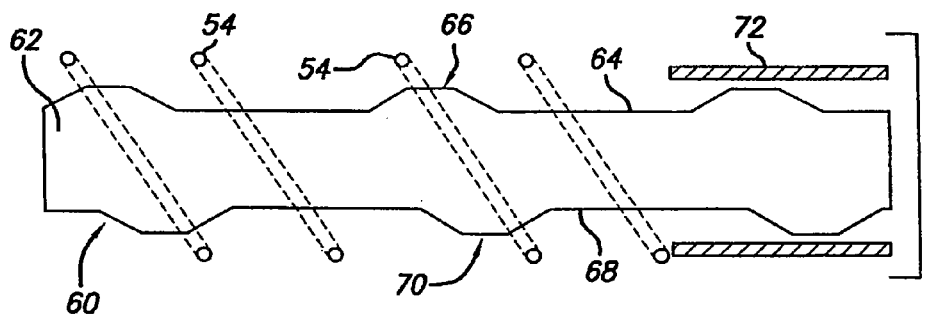
FIG. 17 is a cross-sectional view showing release of the stent from the pusher catheter member of FIG. 16.

In an alternate embodiment illustrated in FIGS. 16 and 17, the stent of the invention may be loaded for delivery on a substantially tubular pusher catheter member 60 having a shaft 62, a plurality of first notches 64 on one side 66 of the shaft, and a plurality of second notches 68 on an opposing side 70 of the shaft of the pusher catheter member, with individual notches of the plurality of second notches typically being offset from corresponding ones of the plurality of first notches. One or more of the stent helical windings or coils can be loaded onto the first and second pluralities of notches, and the pusher catheter member, with the stent loaded and/or pressed into the notched portion of the pusher catheter member, can be loaded into a delivery catheter 72 having an inner diameter 74 that is only slightly larger than the outer diameter 76 of the pusher catheter member, so as to retain the stent on the pusher catheter member, allowing the stent to be advanced through the vasculature of a patient to a site of an aneurysm to be treated. With reference to FIG. 17, when the stent is located at the site to be treated, the delivery catheter can be withdrawn, or the pusher catheter member can be pushed out of the delivery catheter, to release the stent from the pusher catheter member.

From the above, it may be observed that the present invention provides significant benefits to the treatment of vascular malformations, and particularly aneurysms in the neurovasculature. Importantly, the invention is particularly advantageous when used in combination with vasoocclusive devices placed in the aneurysm by intravascular procedures. The stents of the present invention may also find application in the treatment of ischemic diseases.

It will be apparent from the foregoing that while particular forms of the invention have been illustrated and described, various modifications can be made without departing from the spirit and scope of the invention. Accordingly, it is not intended that the invention be limited, except as by the appended claims.

We claim:

1. A system for deploying an intravascular flow modifier and reinforcement device for use in the intravascular treatment of a target site in a patient's vasculature, the system comprising:
    an intravascular flow modifier and reinforcement device including a generally cylindrical frame formed of an elongate resilient wire configured as a series of a plurality of helical windings;
    a substantially tubular pusher catheter member having an inner lumen, a proximal portion, a distal portion, a tubular main shaft, and a notched portion including a plurality of alternating notches and tubular shoulder portions formed in a side of the pusher catheter member, each of said notches receiving a plurality of the plurality of helical windings; and
    a release wire removably threaded through the lumen of the pusher catheter member under said shoulder portions and over said plurality of the plurality of helical windings to retain the plurality of helical windings on said notched portion of said pusher catheter member, said release wire being capable of being withdrawn from said notched portion of said pusher catheter member when the intravascular flow modifier and reinforcement device is positioned at the site in the patient's vasculature to be treated to release and deploy the intravascular flow modifier and reinforcement device at the site in the patient's vasculature to be treated.

2. The system of claim 1, wherein said release wire is formed of a nickel-titanium alloy.

3. The system of claim 1, wherein said generally cylindrical frame consists of a single elongate resilient wire configured as a series of a plurality of helical windings, each of said helical windings including a series of between 4 and 8 alternating zigzag bends in a rotation of the wire, said generally cylindrical frame having a longitudinal axis, a deployed configuration and a predeployed compressed configuration for placement of the intravascular flow modifier and reinforcement device at the target site, said generally cylindrical frame in its deployed configuration having a helical pattern of sharp alternating zigzag bends aligned to have a chevron configuration when viewed from a first direction transverse to the longitudinal axis, and a reverse chevron configuration when viewed from a second direction transverse to the longitudinal axis.

4. The system of claim 3, wherein said deployed configuration comprises a generally cylindrical configuration.

5. The system of claim 3, wherein said predeployed compressed configuration comprises a radially compressed configuration.

6. The system of claim 3, wherein said alternating zigzag bends have an angle that is less than about 120° to promote laminar arterial flow.

7. The system of claim 3, wherein said helical windings have a variable pitch.

8. The system of claim 3, wherein each of said helical windings comprises a series of 4 alternating zigzag bends in a rotation of the wire.

9. The system of claim 3, wherein each of said helical windings comprises a series of 6 alternating zigzag bends in a rotation of the wire.

10. The system of claim 3, wherein said elongate resilient wire is formed of a superelastic material.

11. The system of claim 3, wherein said elongate resilient wire is formed of a shape memory material.

12. The system of claim 3, wherein said elongate resilient wire is formed of a nickel-titanium alloy.

13. The system of claim 3, wherein said elongate resilient wire is coated with a corrosion resistant material.

14. The system of claim 3, wherein said elongate resilient wire is coated with parylene.

15. The system of claim 3, wherein said elongate resilient wire is treated by chemical electropolishing to maximize corrosion resistance.

16. The system of claim 3, wherein said elongate resilient wire comprises a stranded cable including one or more radiopaque strands.

17. The system of claim 3, wherein said elongate resilient wire comprises a stranded cable having radiopaque markers deployed along the said stranded cable.

18. The system of claim 17, wherein said stranded cable is made of a material selected from the group consisting of stainless steel, shape-memory alloy, superelastic alloy, platinum and combinations thereof.

19. The system of claim 3, wherein said elongate resilient wire is formed by laser cutting a piece of tubing.

20. A system for deploying an intravascular flow modifier and reinforcement device for use in the intravascular treatment of a target site in a patient's vasculature, the system comprising:

an intravascular flow modifier and reinforcement device including a generally cylindrical frame formed of an elongate resilient wire configured as a series of a plurality of helical windings;

a substantially tubular pusher catheter member having an inner lumen, a proximal portion, a distal portion, a tubular main shaft, and a notched portion including at least five alternating notches and tubular shoulder portions formed in a side of the pusher catheter member, each of said notches receiving more than one of the plurality of helical windings;

a delivery catheter, and wherein said substantially tubular pusher catheter member and the intravascular flow modifier and reinforcement device received on said notched portion of said pusher catheter member are disposed in the delivery catheter, and wherein said delivery catheter can be withdrawn along with said release wire from said notched portion of said pusher catheter member when the intravascular flow modifier and reinforcement device is positioned at the site in the patient's vasculature to be treated for delivery of the intravascular flow modifier and reinforcement device to the site in the patient's vasculature to be treated; and a release wire removably threaded through the lumen of the pusher catheter member under said shoulder portions and over each of said plurality of helical windings to retain said plurality of helical windings on said notched portion of said pusher catheter member, said release wire being capable of being withdrawn from said notched portion of said pusher catheter member when the intravascular flow modifier and reinforcement device is positioned at the site in the patient's vasculature to be treated to release and deploy the intravascular flow modifier and reinforcement device at the site in the patient's vasculature to be treated.

* * * * *